(12) United States Patent
Zheng (10) Patent No.: US 11,478,219 B2
(45) Date of Patent: Oct. 25, 2022

(54) HANDHELD THREE-DIMENSIONAL ULTRASOUND IMAGING SYSTEM AND METHOD

(71) Applicant: Telefield Medical Imaging Limited, Hong Kong (HK)

(72) Inventor: Yongping Zheng, Hong Kong (HK)

(73) Assignee: Telefield Medical Imaging Limited, Hong Kong (HK)

( * ) Notice: Subject to any disclaimer, the term of this patent is extended or adjusted under 35 U.S.C. 154(b) by 179 days.

(21) Appl. No.: 16/629,955

(22) PCT Filed: Jul. 3, 2018

(86) PCT No.: PCT/CN2018/094306
§ 371 (c)(1),
(2) Date: Jan. 9, 2020

(87) PCT Pub. No.: WO2019/011156
PCT Pub. Date: Jan. 17, 2019

(65) Prior Publication Data
US 2020/0138408 A1    May 7, 2020

(30) Foreign Application Priority Data
Jul. 11, 2017   (CN) .......................... 201710560949.0

(51) Int. Cl.
*A61B 8/00* (2006.01)
*A61B 8/08* (2006.01)

(52) U.S. Cl.
CPC .......... *A61B 8/4427* (2013.01); *A61B 8/4254* (2013.01); *A61B 8/4472* (2013.01);
(Continued)

(58) Field of Classification Search
None
See application file for complete search history.

(56) References Cited

U.S. PATENT DOCUMENTS

2017/0215841 A1* 8/2017 Pandey ................. A61B 8/565

FOREIGN PATENT DOCUMENTS

| CN | 101842053 A | 9/2010 |
|---|---|---|
| CN | 102499762 A | 6/2012 |

(Continued)

OTHER PUBLICATIONS

International Search Report of PCT Patent Application No. PCT/CN2018/094306 dated Sep. 6, 2018.

*Primary Examiner* — Amanda Lauritzen Moher
*Assistant Examiner* — Delia M. Appiah Mensah (57) ABSTRACT

Disclosed in the application is a handheld three-dimensional ultrasound imaging system and method, comprising a handheld ultrasound probe, used for scanning and obtaining an ultrasound image; a display, control and processing terminal, connected to the handheld ultrasound probe wiredly or wirelessly. The handheld ultrasound imaging system and method of the application further comprises: a handheld three-dimensional spatial positioning system, connected to the handheld ultrasound probe, moving with the movement of the handheld ultrasound probe, connected to the display, control and processing terminal wiredly or wirelessly, and used for independently positioning the three-dimensional position of the handheld ultrasound probe. By means of the handheld three-dimensional ultrasound imaging system and method of the present application, the large spatial positioning system in an existing three-dimensional ultrasound imaging system is changed into a portable spatial positioning system that can be used at any time, so that handheld three-dimensional ultrasound imaging can be widely applied.

4 Claims, 3 Drawing Sheets

S1. using a handheld ultrasound probe 100 to scan a part to be tested 600

S2. obtaining a three-dimensional position and angle information corresponding to each ultrasound image through a handheld three-dimensional space positioning system 200

S3. performing 3D image reconstruction to the ultrasound image and the three-dimensional position and angle information and displaying (52) U.S. Cl.
CPC .............. *A61B 8/461* (2013.01); *A61B 8/483* (2013.01); *A61B 8/5215* (2013.01); *A61B 8/56* (2013.01); *A61B 2562/0219* (2013.01)

(56) References Cited

FOREIGN PATENT DOCUMENTS

| | | | |
|---|---|---|---|
| CN | 105025799 | A | 11/2015 |
| WO | 2009149499 | A1 | 12/2009 |

\* cited by examiner

| S1.using a handheld ultrasound probe 100 to scan a part to be tested 600 |
|---|

↓

| S2.obtaining a three-dimensional position and angle information corresponding to each ultrasound image through a handheld three-dimensional space positioning system 200 |
|---|

↓

| S3. performing 3D image reconstruction to the ultrasound image and the three-dimensional position and angle information and displaying |
|---|

Figure 10

HANDHELD THREE-DIMENSIONAL ULTRASOUND IMAGING SYSTEM AND METHOD

TECHNICAL FIELD

The present application relates to the field of medical devices, in particular to a handheld three-dimensional ultrasound imaging system and method.

BACKGROUND

Three dimensional ultrasound imaging has been widely used in the field of medicine. There are usually three ways: electronic scanning, mechanical scanning and manual scanning. Mechanical scanning is to use the motor to drive the ultrasonic probe for scanning, with the advantage of good repeatability, but only suitable for small-scale scanning, such as fetus observation. Electronic scanning can give real-time three-dimensional images, such as the heart, but it is only suitable for scanning in a smaller range, and it needs to use two-dimensional transducer display, making the cost quite expensive. Manual scanning refers to holding the ultrasonic probe by an operator to scan the interested area of human body or animal, recording the three-dimensional spatial position and angle of each ultrasonic image by a spatial positioning system, and then carrying out three-dimensional image reconstruction. Its advantage is that it can do a large range of scanning, but it requires manual scanning.

In recent years, the miniaturization of ultrasound imaging system has developed rapidly. At present, there are many different types of handheld ultrasound systems. By using the handheld ultrasound system, the portability can be greatly improved so that ultrasound imaging can be applied in more fields. However, at present, there is still no handheld three-dimensional ultrasound imaging system in the market, because there are some difficulties in its implementation, especially the palmtop 3D ultrasound imaging system for manual scanning of a large range of human body. Because the traditional ultrasound imaging system requires a large spatial positioning system, which is not suitable for the practical palmtop application. For example, the most commonly used electromagnetic positioning device needs an external transmitter and a spatial positioning sensor placed on the ultrasound probe. It is very difficult to make such a system completely into the palmtop portable system.

Therefore, how to improve the huge spatial positioning system and make the portable handheld three-dimensional ultrasound imaging system widely used has become an urgent technical problem in the industry.

SUMMARY

The purpose of the present application is to provide a handheld three-dimensional ultrasound imaging system and method aiming at the existing technical problems, so that the handheld three-dimensional ultrasound imaging can be widely used.

The technical scheme of the present application for solving the above technical problems is as follows, providing a handheld three-dimensional ultrasound imaging system, comprising a handheld ultrasound probe, used for scanning and obtaining an ultrasound image; a display, control and processing terminal, connected to the handheld ultrasound probe wiredly or wirelessly; the handheld ultrasound imaging system of the present application further comprises: a handheld three-dimensional spatial positioning system, connected to the handheld ultrasound probe, moving with the movement of the handheld ultrasound probe, connected to the display, control and processing terminal wiredly or wirelessly, and used for independently positioning a three-dimensional position and angle information of the handheld ultrasound probe.

Preferably, the handheld ultrasound imaging system further comprises a positioning reference device, located outside the handheld ultrasound probe, used for providing positioning reference for the handheld three-dimensional spatial positioning system.

Preferably, the handheld three-dimensional spatial positioning system is positioned inside the handheld ultrasound probe.

Preferably, the handheld three-dimensional spatial positioning system is an accelerometer or a gyroscope mounted on the handheld ultrasound probe, used for obtaining acceleration or an angular acceleration of the handheld ultrasound probe, and then obtaining a moving distance and a rotation angle of the handheld ultrasound probe.

Preferably, the positioning reference device is a localization image arranged on a part to be tested, and the handheld three-dimensional spatial positioning system comprises a camera used for detecting a position of the localization image and providing positioning reference, and an accelerometer or an gyroscope used for obtaining an acceleration or an angular acceleration of the handheld ultrasound probe and then obtaining a moving distance and a rotation angle of the handheld ultrasound probe.

Preferably, further comprises a cloud database, connected to the display, control and processing terminal communicatively, used for processing the ultrasound image and the three-dimensional position and angle information obtained from the display, control and processing terminal through the wireless or wired data transmission device, and returning data processing results to the display, control and processing terminal.

The present application further provides a handheld three-dimensional ultrasound imaging method, wherein, comprising the following steps:

S1. using a handheld ultrasound probe to scan a part to be tested to obtain a series of ultrasound images;

S2. obtaining a three-dimensional position and angle information corresponding to each frame of ultrasound images through a handheld three-dimensional spatial positioning system;

S3. performing 3D image reconstruction to the ultrasound image and the three-dimensional position and angle information and displaying.

Preferably, the step S3 is:

S3. transmitting the ultrasound image and the three-dimensional position and angle information to a cloud database through a wireless or wired data transmission device for image reconstruction, analysis, calculation and comparison, and the cloud database transmitting results of image reconstruction, analysis, calculation and comparison back to the display, control and processing terminal for display.

Preferably, the step S3 is:

S3. performing 3D image reconstruction to the ultrasound image and the three-dimensional position and angle information and displaying through the display, control and processing terminal.

Preferably, the handheld three-dimensional spatial positioning system is an accelerometer or a gyroscope mounted on the handheld ultrasound probe, used for obtaining an acceleration or an angular acceleration of the handheld ultrasound probe, and then obtaining a moving distance and a rotation angle of the handheld ultrasound probe.

Preferably, the step S2 of the imaging method comprises the following steps:

S2.1 using the three-dimensional spatial positioning system to scan a positioning reference device for providing positioning reference for the handheld three-dimensional spatial positioning system.

Preferably, the positioning reference device is arranged on a part to be tested, the step S3 of the imaging method further comprises the following steps:

S3.1 the display, control and processing terminal extracting information of the positioning reference device from the ultrasound image as positioning information;

S3.2 the display, control and processing terminal restoring the ultrasound image to a state without interference from the positioning reference device, and then performing 3D image reconstruction to the ultrasound image and displaying.

Preferably, positioning reference device is arranged on a part to be tested, the step S1 of the imaging method further comprises the following steps:

S1.1 when the positioning reference device is arranged on the part to be tested, using the handheld ultrasound probe to scan the part to be tested to obtain a first ultrasound image;

S1.2 removing the positioning reference device, and using the handheld ultrasound probe to scan the part to be tested again to obtain a second ultrasound image;

the step S3 of the imaging method further comprises the following steps:

S3.6 the display, control and processing terminal using the first ultrasound image as a reference to determine the position of the positioning reference device relative to the second ultrasound image, thus performing 3D image reconstruction to the ultrasound image and the three-dimensional position and angle information and displaying.

By means of the handheld three-dimensional ultrasound imaging system and method of the present application, the large spatial positioning system in an existing three-dimensional ultrasound imaging system is changed into a portable spatial positioning system that can be used at any time, so that handheld three-dimensional ultrasound imaging can be widely applied.

BRIEF DESCRIPTION OF THE DRAWINGS

The application will be further described in combination with the accompanying drawings and embodiments, in which.

DETAILED DESCRIPTION OF THE PREFERRED EMBODIMENT

In order to enable those skilled in the art to understand the application more clearly, the application will be described in further detail below in combination with the drawings and specific embodiments.

Figure 1:
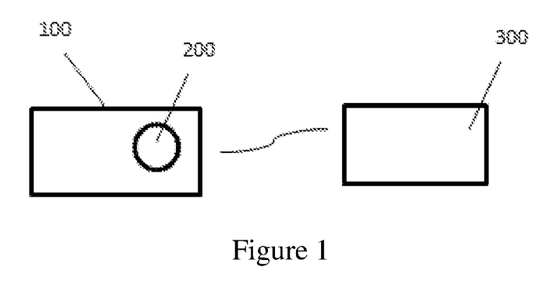
FIG. 1 is the structure diagram of the handheld three-dimensional ultrasound imaging system of the present application.

As shown in FIG. 1, the present application discloses a handheld three-dimensional ultrasound imaging system, comprising a handheld ultrasound probe 100; a display, control and processing terminal 300, connected to the handheld ultrasound probe 100 wiredly or wirelessly; a handheld three-dimensional spatial positioning system 200, connected to the handheld ultrasound probe 100, moving with the movement of the handheld ultrasound probe 100, connected to the display, control and processing terminal 300 wiredly or wirelessly. In FIG. 1, the handheld three-dimensional spatial positioning system 200 is mounted on the handheld ultrasound probe 100. In other embodiments, as long as it is connected with the handheld ultrasound probe 100, it can move with the movement of the handheld ultrasound probe 100, without necessarily being installed on the handheld ultrasound probe 100, and the specific setting mode is not limited here. The display, control and processing terminal 300 of the application can be a palmtop terminal or a desktop terminal, such as a laptop, etc., which can be connected with the handheld ultrasound probe 100 by wireless or wired means. The display, control and processing terminal 300 stores three-dimensional imaging, image processing and three-dimensional display algorithms, which directly analyzes and processes the image and data information returned by the handheld ultrasound probe 100, and displays three-dimensional images.

Figure 2:
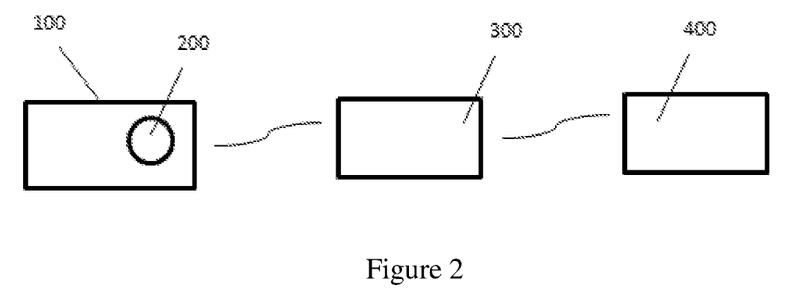
FIG. 2 is the structure diagram of the handheld three-dimensional ultrasound imaging system in a preferred embodiment of the present application.

As shown in FIG. 2, since the handheld three-dimensional ultrasound imaging system is required to be small in size and portable, in order to reduce the dimension of the handheld three-dimensional ultrasound imaging system, the handheld three-dimensional ultrasound imaging system of the present application further includes a cloud database 400 and a similar processing system. Thus, the display, control and processing terminal 300 transmits the three-dimensional position information, angle and reconstruction result to the cloud database 400 for storage. In the cloud database 400, the reconstruction results can be classified and stored, for example, the time can be classified and stored by the name of the customer, so as to facilitate the user to compare the changes of the part to be tested 600 in different time periods, or the classification and storage can be carried out by the name of different diseases, so that the user can refer to the changes of the part to be tested 600 to be detected by other users.

Further, in order to make the handheld three-dimensional ultrasound imaging system more miniaturized and improve its portability, only simple 3D imaging, image processing and 3D display algorithms are stored in the display, control and processing terminal 300, and the image and data information are simply analyzed and processed. The display, control and processing terminal 300 is connected to the cloud database 400 and similar processing systems through the network, Bluetooth and other ways. In the cloud database 400, more advanced and more complex 3D imaging, image processing and 3D display algorithms can be stored. The display, control and processing terminal 300 uploads the simple processed information to the cloud database 400 for analysis and processing. The cloud database 400 transmits the results after analysis and processing back to the display, control and processing terminal 300 of the handheld ultrasonic instrument for display or further processing. Even, the display, control and processing terminal 300 may not store three-dimensional imaging, image processing and three-dimensional display algorithm, just upload the image and data information returned by the handheld ultrasound probe 100 directly to the cloud database 400, and process, analyze and process through the three-dimensional imaging, image processing and three-dimensional display algorithm in the cloud database 400. After that, the information is transmitted back to the display, control and processing terminal 300 for display. Similarly, in the cloud database 400, the reconstruction results can still be classified and stored, so that customers can retrieve the data of the reconstruction results from the cloud database 400 for query. The cloud database 400 can be a remote storage and computing device.

The handheld three-dimensional spatial positioning system 200 in the application is a device convenient for moving and installing, which is connected with the handheld ultrasound probe 100, and can move with the movement of the handheld ultrasound probe 100. The handheld three-dimensional ultrasound imaging system can directly obtain the 3D spatial position of the handheld ultrasound probe 100 through the handheld three-dimensional spatial positioning system 200, without any other positioning system. Preferably, the handheld three-dimensional spatial positioning system 200 is arranged inside the handheld ultrasound probe 100, so that when the handheld three-dimensional ultrasound imaging system of the present application is applied, there will not be a non portable positioning system to affect the portability of the handheld three-dimensional ultrasound imaging system. There are six embodiments of how the handheld three-dimensional spatial positioning system 200 obtains the 3D position information and angle information of the handheld ultrasound probe 100.

Figure 3:
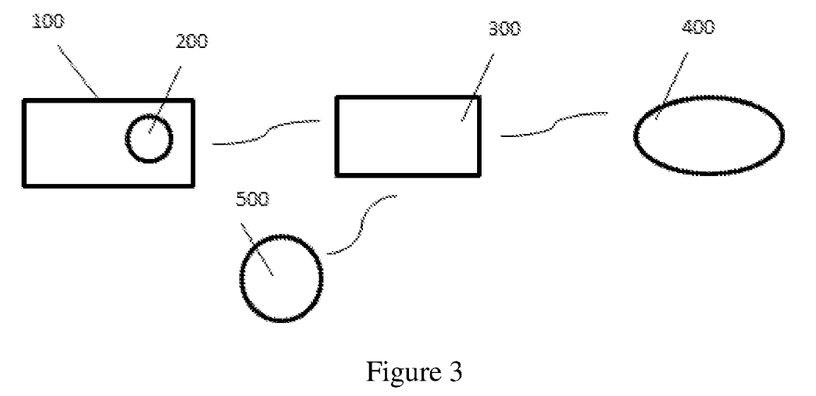
FIG. 3 is the structure diagram of the handheld three-dimensional ultrasound imaging system in another preferred embodiment of the present application.

As shown in FIG. 3, in order to improve the accuracy of positioning, the handheld three-dimensional ultrasound imaging system can further include a positioning reference device 500, which is located outside the handheld ultrasound probe 100 and is used to provide positioning reference for the handheld three-dimensional spatial positioning system 200.

The First Embodiment

The handheld three-dimensional spatial positioning system 200 includes micro inertial sensors such as accelerometers and angular velocity meters installed on the handheld ultrasound probe 100, which are used to obtain the acceleration and angular acceleration values of the handheld ultrasound probe 100, so as to calculate the moving distance and rotation angle of the handheld ultrasound probe 100, and then independently obtain the 3D spatial position of the handheld ultrasound probe 100.

The Second Embodiment

The handheld three-dimensional spatial positioning system 200 includes one or more cameras installed on the handheld ultrasound probe 100 and micro inertial sensors such as accelerometers, angular velocity meters installed in the handheld ultrasound probe 100. The positioning reference device 500 is an external environment. The camera is used to obtain the image of the surrounding environment, such as the grid on the ceiling, etc. according to the obtained image changes, the position and angle of the handheld ultrasound probe 100 can be calculated, and special graphics can also be simply added in the environment to facilitate detection. Accelerometers and angular velocity meters are used to obtain the acceleration and angular acceleration values of the handheld ultrasound probe 100, so as to calculate the moving distance and angle of the handheld ultrasound probe 100. The combination of accelerometer, angular velocity meter and camera makes the positioning more accurate. Before using the handheld three-dimensional spatial positioning system 200, it is necessary to let the handheld ultrasound probe 100 move a known distance or rotate a known angle to determine the parameters needed in the positioning algorithm.

The Third Embodiment

Figure 4:
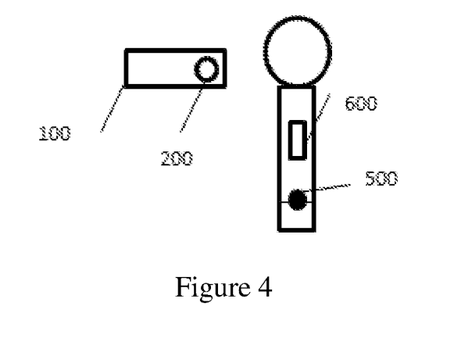
FIG. 4 is the structure diagram of the handheld three-dimensional ultrasound imaging system in a third embodiment of the present application.

As shown in FIG. 4, the handheld three-dimensional spatial positioning system 200 is a micro inertial sensor, such as accelerometer and gyroscope, which are installed on the handheld ultrasound probe 100. The handheld three-dimensional ultrasound system further includes a positioning reference device 500, which is a small reference system installed on or near the scanning object, i.e. installed outside the handheld ultrasound probe 100, and is used to provide positioning reference for the handheld three-dimensional spatial positioning system 200. The miniaturized reference system is a miniaturized electromagnetic transmitter installed on the scanning object. In addition to the electromagnetic transmitter, the sound or light transmitting and receiving system can also be used, that is, the miniaturization of the traditional light, sound and electromagnetic handheld three-dimensional spatial positioning system. Accelerometers and gyroscope are used to obtain the acceleration and angular acceleration values of the handheld ultrasound probe 100, so as to calculate the moving distance and angle of the handheld ultrasound probe 100. The combination of accelerometer, angular velocity meter and small reference system makes the positioning more accurate.

In addition, the small reference system can also be one or more micro cameras placed on the scanning body, recording the rotation angle of the micro camera to track the movement and angle of the probe.

The Fourth Embodiment

The handheld three-dimensional spatial positioning system 200 in the fourth embodiment is a micro inertial sensor such as an accelerometer, a gyroscope, etc. The handheld three-dimensional ultrasound system further includes a positioning reference device 500, which is the ultrasound image itself.

Figure 5A:
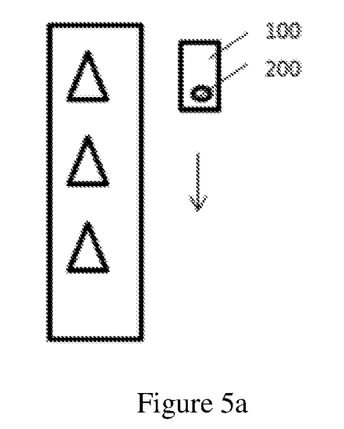
FIG. 5a is the scanning diagram of the handheld three-dimensional ultrasound imaging system in a fourth embodiment of the present application.
Figure 5B:
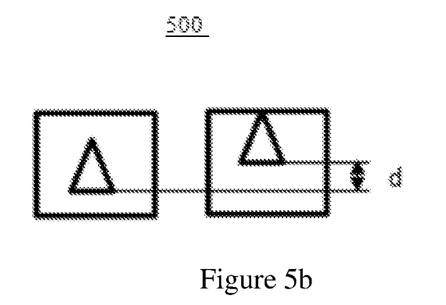
FIG. 5b is a schematic diagram of two consecutive ultrasound images in the fourth embodiment of the present application.

As shown in FIG. 5*a*, when the handheld ultrasound probe 100 moves, the left and right ultrasound images in FIG. 5*b* are obtained successively. The two ultrasound images have continuity and some overlapped parts, that is, the content of the ultrasound images obtained sequentially has great similarity. When the image sampling speed is very high, but the moving speed is not very fast, the difference distance d between the two images can be obtained by the way of image matching, and the moving distance can be obtained by the difference between the successively obtained ultrasound images. In the same way, the rotation angle of the handheld ultrasound probe 100 in this plane can also be obtained. However, when the ultrasound image itself is used alone, the limitation is that the handheld ultrasound probe 100 can only move or rotate in one direction. When the handheld ultrasound probe 100 moves or rotates in the reverse direction, it is easy to cause the calculation error of the collected three-dimensional position information or angle information.

Therefore, in this embodiment, micro inertial sensors such as accelerometers and angular velocity meter are used in combination with ultrasound images, and micro inertial sensors such as accelerometers and angular velocity meter are used to obtain the acceleration and angular acceleration values of the handheld ultrasound probe 100, so as to calculate the moving distance and angle of handheld ultrasound probe 100, which can supplement the data obtained from the images, making the positioning method more accurate.

The Fifth Embodiment

The difference between the fifth embodiment and the fourth embodiment is that the handheld ultrasound probe of the fifth embodiment uses a compound probe, that is, a sub probe in different directions is installed in one handheld ultrasound probe 100, which is used to measure the moving distance and rotation angle of the handheld ultrasound probe 100 in both directions at the same time. The handheld three-dimensional spatial positioning system 200 is still a micro inertial sensor such as accelerometer and gyroscope. It is used to obtain the acceleration and angular acceleration values of the handheld ultrasound probe 100, and calculate the moving distance and angle of the handheld ultrasound probe 100. Thus, the handheld three-dimensional spatial positioning system 200 can detect the amount of movement and rotation in the third direction besides the direction provided by the compound probe, and then calculate the 3D position information and angle of the handheld ultrasound probe 100 more accurately.

The Sixth Embodiment

Figure 6:
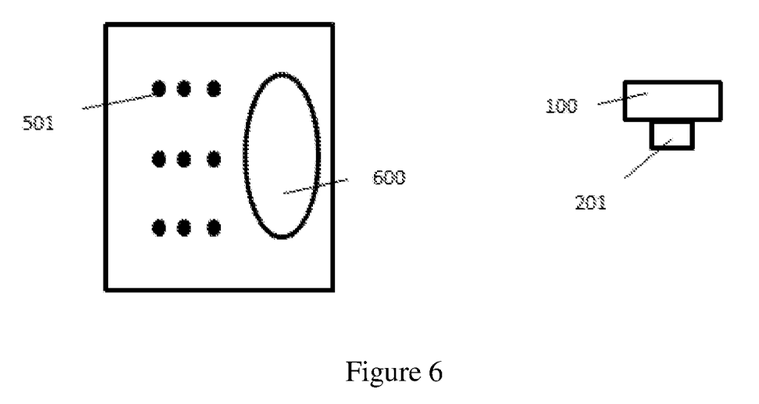
FIG. 6 is the structure diagram of the positioning reference device and the handheld ultrasound probe in a sixth embodiment of the present application.

As shown in FIG. 6, the handheld three-dimensional ultrasound imaging system further includes a positioning reference device 500, in this embodiment, the positioning reference device 500 is a localization image 501 set on the surface of the scanning object. The handheld three-dimensional spatial positioning system 200 includes a camera 201 mounted on the handheld ultrasound probe 100. When the handheld ultrasound probe 100 moves, the camera 201 tracks the moving distance and rotation angle of the handheld ultrasound probe 100 according to the change of the localization image 501. Preferably, the handheld three-dimensional spatial positioning system 200 also includes micro inertial sensors such as accelerometers and gyroscope installed on the handheld ultrasound probe 100 for further providing information about the moving distance and rotation angle of the handheld ultrasound probe 100. The localization image 501 may be a specially designed image temporarily pasted on the surface of the scanning object, and they are pasted beside the part to be tested 600 of the object to be scanned, so as to avoid the interference of the localization image 501 on the ultrasonic signal. In this embodiment, the localization image 501 is a lattice attached to the part to be tested 600, and the distance between the points in the lattice is a pre-designed value, which is known. Preferably, the lattice can also be designed as points with large and small intervals, which can be used to provide a clearer positioning reference.

In this embodiment, the camera 201 is used to record the localization image 501 for positioning. In other embodiments of the application, other similar methods can be applied, for example, the localization image 501 with the characteristics of sound, light, electrical, magnetic, etc. is designed and pasted on the scanning object, and a detector is installed on the handheld ultrasound probe 100 to record the localization image 501 located outside the part to be tested 600 for positioning.

The Seventh Embodiment

The difference between the seventh embodiment and the sixth embodiment is that the localization image 501 of the sixth embodiment is temporarily attached to the part to be tested 600 of the object to be scanned, that is, the ultrasound will not scan the localization image 501 to avoid interference of the localization image 501 with the ultrasonic signal. However, in the sixth embodiment, the interference of the localization image 501 with the ultrasonic signal is used for positioning.

Figure 7:
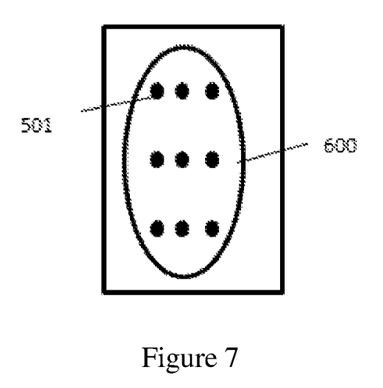
FIG. 7 is the structure diagram of the positioning reference device in a seventh embodiment of the present application.
Figure 8A:
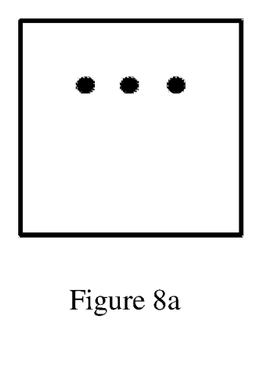
FIG. 8a is a positioning information diagram obtained by scanning positioning reference device in the seventh embodiment of the present application.
Figure 8B:
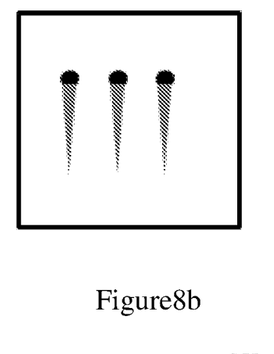
FIG. 8b is another positioning information diagram obtained by scanning positioning reference device in the seventh embodiment of the present application.

As shown in FIG. 7, the localization image 501 is a lattice, of course, in other embodiments of the application, the localization image 501 can also be of other shapes, such as lattice, wave shape, etc., as long as it can provide positioning reference. The localization image 501 in the embodiment is pasted on the part to be tested 600, and the distance between the points in the lattice is a pre-designed value, which is known. Preferably, the setting mode can be a mode with one big point for every five small points to provide positioning information more clearly. Further, according to the material of the localization image 501, each point on the lattice has different degrees of influence on the ultrasonic signal. As shown in FIG. 8*a*, the reflection signal can be a point, as shown in FIG. 8*b*, and the reflection signal can also be a point with a shadow area, which is used to distinguish the position of each row or column of points, so as to make the positioning more accurate. Preferably, the localization image 501 is integrated with the ultrasonic coupling paste, which makes the use and attachment on body surface easier and the operation process more concise.

Therefore, in this embodiment, there are two positioning methods. The first method is to extract the information of the localization image 501 from the obtained ultrasound image as positioning information, then recover the ultrasound image to a state without interference of the localization image 501 after image processing, and then reconstruct the three-dimensional image of the ultrasound image.

Another positioning method is to scan the part to be tested 600 once when the localization image 501 is attached on the part to be tested 600 to obtain the first ultrasound image, the scope of the first ultrasound image may include the localization image 501 and the scope beyond the localization image 501; then take away the localization image 501, and then scan again to obtain the second ultrasound image; the display, control and process terminal determines the position of the localization image 501 relative to the second ultrasound image according to the obtained first ultrasound image as a reference, so as to obtain a three-dimensional image which is completely free from the influence of the localization image 501 and has positioning information of the localization image 501.

Figure 9:
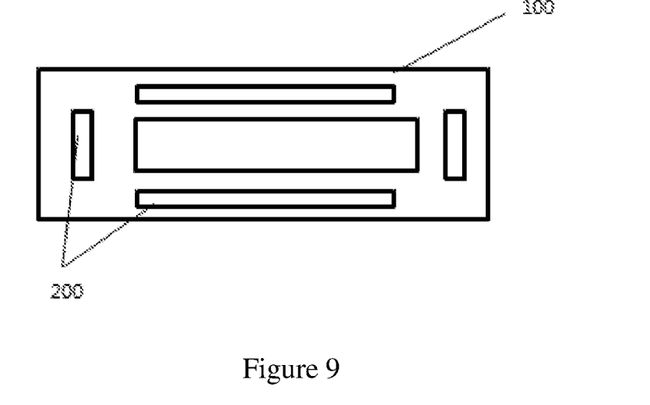
FIG. 9 is the structure diagram of the handheld ultrasound probe of another embodiment of the present application.

As shown in FIG. 9, the above localization image 501 is used in the embodiment to interfere with ultrasonic wave for positioning. In other embodiments of the application, other similar methods can be applied, such as designing localization image 501 with optical, electrical, magnetic and other characteristics, attaching it to the scanning object, and installing optical, electrical, magnetic and other detectors on the handheld ultrasound probe 100 as the palm of the system The localization image 501 is detected by the handheld three-dimensional spatial positioning system 200, and the installation mode of the handheld three-dimensional spatial positioning system 200 is shown in the figure.

It can be understood that in the first to seventh embodiments, all the handheld three-dimensional spatial positioning system 200 installed on the handheld ultrasound probe 100, i.e. camera, sound, light, electrical, magnetic detector, etc., may not be installed on the handheld ultrasound probe 100, as long as they can move with the movement of the handheld ultrasound probe 100, there is no limit here.

Figure 10:
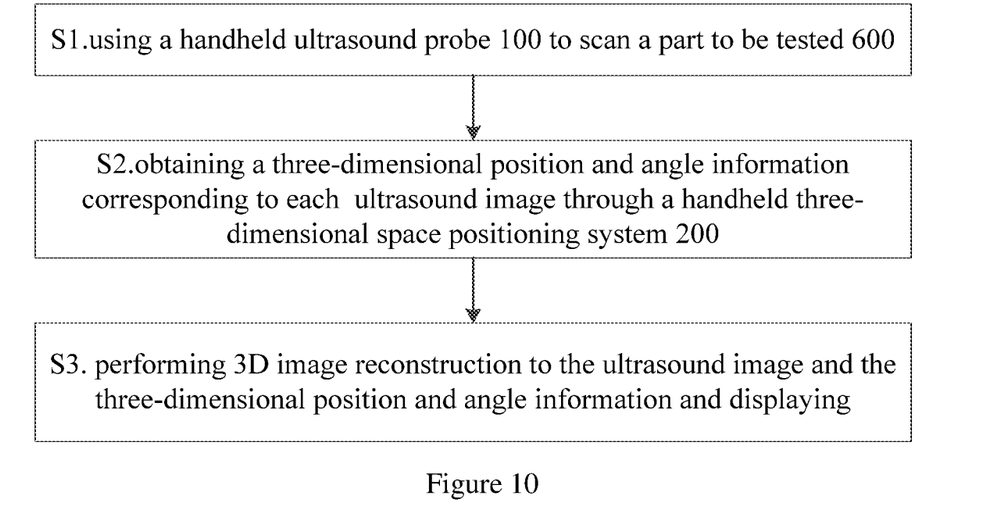
FIG. 10 is the diagram of the handheld three-dimensional ultrasound imaging of the present application.

As shown in FIG. 10, the present application further discloses a handheld three-dimensional ultrasound imaging method, comprising the following steps:

S1. using a handheld ultrasound probe 100 to scan a part to be tested 600 to obtain a series of ultrasound images;

S2. obtaining a three-dimensional position and angle information corresponding to each frame of ultrasound images through a handheld three-dimensional spatial positioning system 200;

S3. performing 3D image reconstruction to the ultrasound image and the three-dimensional position and angle information and displaying.

In the handheld three-dimensional ultrasound imaging method, the step S2 comprises the following steps:

S2.1 arranging a positioning reference device 500 on the scanning objects for providing positioning reference for the handheld three-dimensional spatial positioning system 200.

The positioning reference device 500 is an electrical, magnetic, acoustic, optical and other transmitters installed on the scanning object, and the transmitted electrical, magnetic, acoustic, optical and other signals can be received by the corresponding receiver installed on the handheld ultrasound probe 100 for positioning reference; or place the localization image 501 with electrical, magnetic, acoustic and optical characteristics on the surface of the scanning object, so that it can be detected by the ultrasonic transducer on the handheld ultrasound probe 100, or the electrical, magnetic, acoustic and optical detectors, and then used for positioning. For specific embodiments, please refer to the first to sixth embodiments, which will not be described here.

In the handheld three-dimensional ultrasound imaging method, the step S3 comprises the following steps:

S3.1 performing 3D image reconstruction to the ultrasound image and the three-dimensional position and angle information and displaying through the display, control and processing terminal 300.

In order to realize the miniaturization of the handheld three-dimensional ultrasound imaging system, when the handheld three-dimensional ultrasound imaging system further includes the cloud database 400 for storing data, step S3 further includes:

S3.2 The display, control and processing terminal 300 transmits the reconstruction result to the cloud database 400 for storage.

In the cloud database 400, the reconstruction results can be classified and stored, for example, the time can be classified and stored by the name of the customer, so as to facilitate the user to compare the changes of the part to be tested 600 in different time periods, or the classification and storage can be carried out by the name of different diseases, so that the user can refer to the changes of the part to be tested 600 by other users.

In order to realize further miniaturization and portability of the handheld three-dimensional ultrasound imaging system, the handheld three-dimensional ultrasound imaging system further includes a cloud database 400 for data processing, and the steps S3 of the imaging method include:

S3.3 the display, control and processing terminal 300 transmits the ultrasound image and the three-dimensional spatial information and angle to the cloud database 400;

S3.4 the cloud database 400 performs 3D image reconstruction of the ultrasound image and the 3D spatial information and angle, and transmits the reconstruction result back to the display, control and processing terminal 300;

S3.5 the display, control and processing terminal 300 displays the reconstruction result.

Similarly, in the cloud database 400, the reconstruction results can be classified and stored, so that customers can retrieve the data of the reconstruction results from the cloud database 400 for query.

The handheld three-dimensional spatial positioning system 300 in the method can be any of the handheld three-dimensional spatial positioning system in the first to seventh embodiments, and the positioning reference device 500 of the application can be any of the positioning reference devices in second to seventh embodiments; when the positioning reference device 500 is the material shown in the seventh embodiment, which is a material that can interfere with ultrasound imaging, and is disposed on the part to be tested 600, the step S3 of the imaging method further includes the following steps:

S3.1 the display, control and processing terminal 300 extracting information of the positioning reference device 500 from the ultrasound image as positioning information;

S3.2 the display, control and processing terminal 300 restoring the ultrasound image to a state without interference from the positioning reference device 500, and then performing 3D image reconstruction to the ultrasound image and displaying.

In the seventh embodiment, there is another positioning method. Step S1 of the imaging method further includes the following steps:

S1.1 when the positioning reference device 500 is arranged on the part to be tested 600, using the handheld ultrasound probe 100 to scan the part to be tested 600 to obtain a first ultrasound image;

S1.2 removing the positioning reference device 500, and using the handheld ultrasound probe 100 to scan the part to be tested 600 again to obtain a second ultrasound image;

Meanwhile, step S3 of the imaging method further includes the following steps:

S3.6 the display, control and processing terminal 300 using the first ultrasound image as a reference to determine the position of the positioning reference device 500 relative to the second ultrasound image, thus performing 3D image reconstruction to the ultrasound image and the three-dimensional position and angle information and displaying.

To sum up, a handheld three-dimensional ultrasound imaging system and method disclosed by the application do not use the traditional large-size and bulky spatial positioning system to locate the handheld ultrasound probe, instead use the portable handheld three-dimensional spatial positioning system and positioning reference device, or even the handheld three-dimensional spatial positioning system alone. It is convenient for users to carry and use the handheld three-dimensional ultrasound imaging system disclosed by the application at any time, and a miniaturized and portable handheld three-dimensional ultrasound imaging system is achieved.

It should be understood that for those of ordinary skill in the art, improvements or transformations can be made according to the above description, and all of these improvements and transformations belong to the scope of protection of the appended claims of the application.

What is claimed is:

1. A handheld three-dimensional ultrasound imaging system, comprising a handheld ultrasound probe, used for scanning and obtaining an ultrasound image;
    a display, control and processing terminal connected to the handheld ultrasound probe wired or wirelessly;
    further comprising:
    a handheld three-dimensional spatial positioning system, connected to the handheld ultrasound probe, moving with movement of the handheld ultrasound probe, connected to the display, a control and processing terminal wired or wirelessly connected to the handheld three-dimensional spatial positioning system and used for generating a three-dimensional position and angle information of the handheld ultrasound probe according to a positioning reference device adapted to be arranged on a part to be tested, wherein the positioning reference device comprises a localization pattern;
    and wherein the handheld three-dimensional spatial positioning system obtains a moving distance and a rotation angle of the handheld ultrasound probe according to a material interference of the localization pattern with the ultrasonic signal;
    a display, control and processing terminal are configured to extract information of the localization pattern from the ultrasound image as positioning information;
    and wherein the display, control and processing terminal are configured to restore the ultrasound image to a state without interference from the localization pattern, and further configured to perform 3D image reconstruction and display of the ultrasound image.

2. The handheld three-dimensional ultrasound imaging system according to claim 1, wherein, the handheld three-dimensional spatial positioning system is positioned inside the handheld ultrasound probe.

3. The handheld three-dimensional ultrasound imaging system according to claim 1, wherein, the handheld three-dimensional spatial positioning system comprises a camera arranged on the handheld ultrasound probe.

4. The handheld three-dimensional ultrasound imaging system according to claim 1, further comprising a cloud database communicatively connected to the display, control and processing terminal and configured to process the ultrasound image to obtain three-dimensional position and angle information through a wireless or wired transmission device, and further configured to return data processing results to the display, control and processing terminal.

* * * * *